United States Patent [19]
Lesk et al.

[11] Patent Number: 5,434,442
[45] Date of Patent: Jul. 18, 1995

[54] FIELD PLATE AVALANCHE DIODE

[75] Inventors: Israel A. Lesk, Phoenix; Hassan Pirastehfar, Mesa, both of Ariz.

[73] Assignee: Motorola, Inc., Schaumburg, Ill.

[21] Appl. No.: 884,319

[22] Filed: May 11, 1992

Related U.S. Application Data

[63] Continuation of Ser. No. 546,638, Jul. 2, 1990, abandoned.

[51] Int. Cl.⁶ .................................... H01L 29/90
[52] U.S. Cl. ..................................... 257/367
[58] Field of Search .............. 357/13, 53, 54, 23.13, 357/25; 257/367

[56] References Cited

U.S. PATENT DOCUMENTS

| | | | |
|---|---|---|---|
| 3,560,810 | 2/1971 | Balk et al. | 357/23.15 |
| 4,103,227 | 7/1978 | Zemel | 357/25 |
| 4,115,709 | 9/1978 | Inoue et al. | 357/23.13 |
| 4,193,935 | 2/1979 | Bertin et al. | 357/23.13 |
| 4,868,621 | 9/1989 | Miyamoto | 357/23.13 |
| 4,987,465 | 1/1991 | Longcor et al. | 357/23.13 |

*Primary Examiner*—William D. Larkins
*Attorney, Agent, or Firm*—Jackson:Miriam

[57] ABSTRACT

A field plate avalanche diode has a field plate extending over the breakdown PN junction.

11 Claims, 1 Drawing Sheet

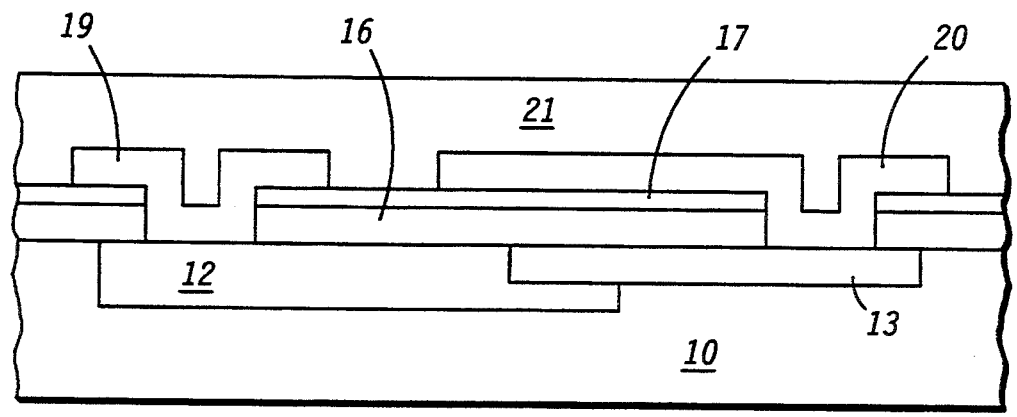
FIG. 1
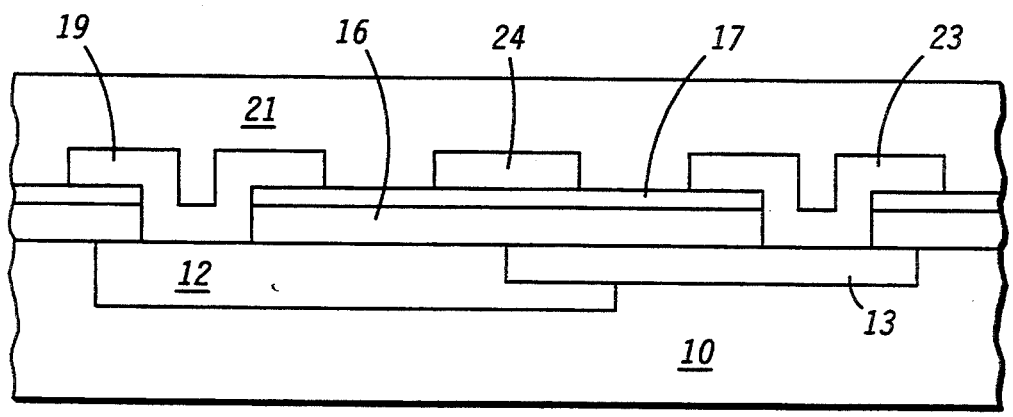
FIG. 2
FIG. 3
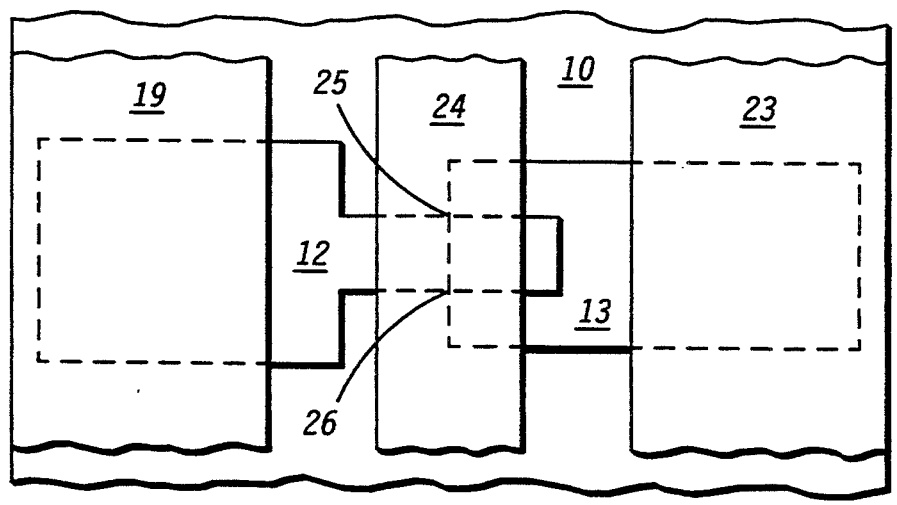

5,434,442

FIELD PLATE AVALANCHE DIODE

This application is a continuation of prior application Ser. No. 07/546,638, filed Jul. 2, 1990, now abandoned.

BACKGROUND OF THE INVENTION

This invention relates, in general, to semiconductor devices, and more particularly, to a semiconductor device used for detecting hydrogen.

It would be desirable to be able to detect the amount of hydrogen present in an ambient for safety reasons, among others. It would also be desirable to be able to detect the amount of hydrogen that is present in a semiconductor device. Hydrogen is introduced into the semiconductor device during and subsequent to processing. It is known that hydrogen affects the avalanche voltage of a P-N junction, however, the mechanism has not been well understood.

In the past, the presence of hydrogen has been detected by porous membrane hydrogen detectors. Porous membrane hydrogen detectors allow only hydrogen to go through them, thus the amount of hydrogen can be measured. Palladium membranes have been placed on top of MOS devices in the past. This method, however, is undesirable because it is not reproducible and stable. In addition, porous membrane hydrogen detectors measure just the total amount of hydrogen in the ambient. However, once the hydrogen has diffused into the semiconductor device, a certain amount of hydrogen may be trapped beneath certain layers, such as nitride layers of the semiconductor device. Some of the hydrogen will also be bound by a nitride layer. Thus, it would be desirable to be able to detect the amount of unbound hydrogen in the semiconductor device, because that is the hydrogen that causes a change in the avalanche voltage of the device. Furthermore, it would be desirable to be able to clear or reset the device of any hydrogen or other interfering atoms or ions that are introduced into the device during manufacturing or anytime thereafter. Once cleared or reset, the device can be used to detect the amount of hydrogen in air or other gaseous mixtures.

Another way to measure the total content of hydrogen present in a semiconductor device is by the use of Secondary Ion Mass Spectroscopy (SIMS). Although this technique is accurate, it is expensive and destructive, and typically the semiconductor device must be sent out to a lab to have the analysis done. It would be desirable to be able to detect the presence of hydrogen quickly and inexpensively.

Accordingly, it is an object of the present invention to provide a method and device for detecting hydrogen.

Another object of the present invention is to provide a hydrogen detector having electrical reset capability.

An additional object of the present invention is to provide a hydrogen detector that detects unbound hydrogen that causes degradation in device characteristics.

A further object of the present invention is to provide a hydrogen detector that can be cleared of interfering elements before operation.

Yet another object of the present invention is to provide a hydrogen detector that can detect the amount of hydrogen in air or other gaseous mixtures.

SUMMARY OF THE INVENTION

The above and other objects and advantages of the present invention are achieved by reverse biasing a semiconductor device having a conductive layer overlay across a P-N junction of the device. The overlay structure increases the sensitivity of the device to hydrogen. Thus, a change in measured avalanche voltage may be directly correlated to the amount of hydrogen present. The device can also be electrically reset after a measurement. The conductive layer overlay may be split up to provide a separate conductive layer positioned over the P-N junction. This conductive layer may be separately biased, so that the device may be cleared of hydrogen, as well as interfering alkali atoms, before operation starts.

BRIEF DESCRIPTION OF THE DRAWINGS

FIG. 1 illustrates an enlarged, cross-sectional view of an embodiment of a structure used to carry out the present invention;

FIG. 2 illustrates an enlarged, cross-sectional view of an embodiment of the present invention; and FIG. 3 illustrates a top view of certain layers of an embodiment of the present invention.

DETAILED DESCRIPTION OF THE INVENTION

FIG. 1 illustrates an embodiment of a structure used to carry out the present invention. What is shown is a substrate 10 of a first conductivity type. A first doped region 12 of the first conductivity type is formed in substrate 10. A second doped region 13 of a second conductivity type is formed in substrate 10 and partially overlapping first doped region 12. The first conductivity type is P-type and the second conductivity type is N-type. If the conductivities are reversed, the method of the present invention can not be carried out. The first and second doped regions 12 and 13 are formed in substrate 10 using standard ion implantation or diffusion techniques. First doped region 12 is preferably doped with boron. First and second doped regions 12 and 13 form a zener diode. As a result of processing first and second doped regions 12 and 13, an insulating layer 16 is formed on the surface of substrate 10 over first doped region 12 and second doped region 13. A phosphorous doped insulating layer 17 is formed on insulating layer 16. Alternatively, layers 16 and 17 may be formed subsequently to the formation of first and second doped regions 12 and 13. In a preferred embodiment, insulating layer 16 is a silicon dioxide layer and phosphorous doped insulating layer 17 is a phosphorous doped glass or a phosphosilicate glass (PSG) which is heavily doped. Insulating layer 16 and phosphorous doped insulating layer 17 are then patterned to provide openings over first doped region 12 and second doped region 13. The patterning is accomplished by standard photolithography and etch processes well known in the art.

Next, a conductive layer is formed on the surface of phosphorous doped insulating layer 17 and in openings of phosphorous doped insulating layer 17 and insulating layer 16. As described in this invention, a conductive layer encompasses either a conductive layer or a semiconductive layer, such as a metal layer or a polysilicon layer. This conductive layer is then patterned to form a first conductive layer 19 which makes contact to first doped region 12, and a second conductive layer 20 which makes contact to second doped region 13 and overlays both first doped region 12 and second doped region 13 (the P-N junction). Commonly, a passivation layer 21 is subsequently deposited over the whole surface. Passivation layer 21 may be comprised of a phosphorous doped glass, a phosphorous glass and a silicon nitride layer, or other passivation materials. If a silicon nitride layer is used as passivation layer 21, the silicon nitride will act as a cap, trapping any hydrogen that was introduced during processing of the semiconductor device. For detecting ambient hydrogen, passivation layer 21 can not include a hydrogen blocking layer such as a nitride layer.

With reference to FIG. 1, a method of detecting hydrogen is accomplished as follows: first and second doped regions 12 and 13 are reverse biased into avalanche. Hot electron current then flows through insulating layer 16. When ambient hydrogen atoms enter insulating layer 16, those hydrogen atoms that migrate near the avalanche region, the interface between first doped region 12 and second doped region 13 and near the interface of insulating layer 16, will experience hot electron impact and will ionize and drift into first doped region 12. Upon drifting into first doped region 12, the hydrogen will disrupt some boron acceptor bonds and form boron-hydrogen bonds, which are not acceptors, and thereby increase the avalanche voltage of the device. By having conductive layer 20 overlay the interface between first doped region 12 and second doped region 13, the avalanche region, the sensitivity of the device to hydrogen is increased. The change in avalanche voltage can then be correlated to the amount of unbound hydrogen present in the device. Any bound hydrogen does not affect the avalanche voltage and is not detected.

The avalanche voltage will increase with an increase in the surface resistivity of first doped region 12 as manufactured. This will increase the sensitivity of the device to hydrogen, however, there is a compromise. With a higher resistivity first doped region 12, operating power will be higher for the same operating current in avalanche. In addition, junction temperature will increase, and if high enough, will cause some thermal annealing of boron neutralization bonds. The surface resistivity of first doped region 12 is preferably in the range of approximately 0.5 to 0.001 ohm-cm.

Reset can be accomplished by applying a forward bias between conductive layer 19 and conductive layer 20 or 23. This forward biases the P-N junction. Electrons injected into first doped region 12 will recombine with holes. The energy given off by the recombination can break a boron-hydrogen complex and restore it to its original status as an acceptor, with the loose hydrogen free to migrate. Thus, the avalanche voltage of the device will be reset. Reset can be accomplished in a time less than one minute.

FIG. 2 illustrates a second embodiment of the present invention. This embodiment is similar to the structure shown in FIG. 1 which is used to carry out a method of the present invention, however, this embodiment is capable of electrical clear as well as reset. The layers shown in FIG. 2 that are the same as shown in FIG. 1 are referenced by the same numerals. The structure shown in FIG. 1 differs from the structure shown in FIG. 2 in that second conductive layer 20 shown in FIG. 1 is patterned to form two layers—a second conductive layer 23 which makes contact to second doped region 13, and a third conductive layer or field plate 24 positioned to overlay both first doped region 12 and second doped region 13 (the P-N junction).

FIG. 3 illustrates a top view of certain layers of the structure of the present invention as shown in FIG. 2. For illustrative purposes, only first doped region 12, second doped region 13, first conductive layer 19, second conductive layer 23, field plate 24, and substrate 10 are shown. FIG. 3 is included in order to show clearly how first doped region 12 and second doped region 13 overlap. First doped region 12, along with substrate 10 completely surround second doped region 13. Because first doped region 12 has a lower resistivity adjacent to the interface of insulating layer 16 than substrate 10, avalanche occurs along a line 25–26. By adjusting geometries of first and second doped regions 12 and 13, the length and shape of line 25–26 may be varied to change the effective area of the surface avalanche region.

Alkali or hydrogen atoms or ions in insulating layer 16 introduced during manufacturing of the device will interfere with the measurement of ambient hydrogen concentration. To electrically clear the device shown in FIG. 2, a negative bias is placed on field plate 24 with respect to conductive layers 19 and 23, which are tied together to provide a high electric field across insulating layer 16 and phosphorous doped insulating layer 17. The electric field must be high enough so that some electrons pass through insulating layer 16 and phosphorous doped insulating layer 17 from field plate 24 to substrate 10. These hot electrons ionize hydrogen so it can drift to and into field plate 24. Alkali atoms may likewise be ionized and drifted into phosphorus doped insulating layer 17 where they are immobilized, while hydrogen atoms are ionized and drifted into field plate 24, where hydrogen atoms are neutralized and are not subsequently affected by the high field. It is preferable for phosphorus doped insulating layer 17 to be heavily doped in order to more efficiently immobilize alkali atoms. Clearing of these interfering elements may be accomplished in less than one hour. To then detect hydrogen, field plate 24 is connected to conductive layer 23, and operated as described with reference to FIG. 1. Reset is also accomplished in the same manner.

The present invention thus provides a method for the measurement of hydrogen in the ambient, and the measurement of unbound hydrogen in a semiconductor device trapped beneath a capping layer such as a nitride layer. A novel semiconductor device that can detect hydrogen is also provided. An embodiment of the device will also have electrical clear and reset capability. The hydrogen detector may be operated in unpackaged form if shielded from gross contamination, but could also be housed in a package that allows hydrogen to diffuse through it, such as a plastic package. The device may also be housed in a hermetic package with a window that allow hydrogen to diffuse though it. The method of detecting hydrogen is inexpensive and convenient.

We claim:

1. A semiconductor device, comprising:
   a substrate of a P-type conductivity having a top surface;
   a first doped region of a P-type conductivity formed in the substrate extending from the top surface down into the substrate;
   a second doped region of an N-type conductivity formed in the substrate extending from the top surface down into the substrate, wherein the first doped region and the second doped region partially overlap each other at the top surface of the substrate;

an insulating layer disposed on the substrate, the insulating layer having openings over a portion of the first doped region and over a portion of the second doped region;

a phosphorus doped insulating layer disposed on the insulating layer;

a first conductive layer disposed on the substrate in the opening over the portion of the first doped region, and partially disposed on the phosphorus doped insulating layer;

a second conductive layer disposed on the substrate in the opening over the portion of the second doped region, and partially disposed on the phosphorus doped insulating layer; and a third conductive layer disposed on the phosphorus doped insulating layer over the first and the second doped regions, wherein the third conductive layer can be separately biased with respect to the first conductive layer and the second conductive layer.

2. The semiconductor device of claim 1 wherein the first, second and third conductive layers are comprised of polysilicon.

3. The semiconductor device of claim 1 wherein the first, second and third conductive layers are comprised of a metal.

4. The semiconductor device of claim 1 wherein the first doped region has a surface resistivity less than 0.5 ohm-cm.

5. The semiconductor region of claim 1 wherein the phosphorus doped insulating layer is comprised of a phosphosilicate glass.

6. A diode, comprising:

a P-doped region and an N-doped region formed in a P-type semiconductor substrate, wherein the P-doped region and the N-doped region partially overlap each other at the top surface of the semiconductor substrate;

a first conductive layer disposed on the P-doped region;

a second conductive layer disposed on the N-doped region; and a third conductive layer disposed over a portion of the P-doped region and the N-doped region where the P-doped region partially overlaps the N-doped region, wherein the third conductive layer can be separately biased with respect to the first conductive layer and the second conductive layer.

7. A semiconductor device, comprising:

a P-doped region and an N-doped region formed in a P-type semiconductor substrate, wherein the P-doped region and the N-doped region partially overlap each other at the top surface of the semiconductor substrate;

a first conductive layer disposed on the P-doped region;

a second conductive layer disposed on the N-doped region and extends over a portion of the P-doped region.

8. The semiconductor device of claim 7 wherein the first and second conductive layers are comprised of polysilicon.

9. The semiconductor device of claim 1 wherein the first, second and third conductive layers consist essentially of polysilicon.

10. The semiconductor device of claim 7 wherein the P-doped region has a surface resistivity less than 0.5 ohm-cm.

11. The semiconductor device of claim 7 wherein the first and second conductive layers consist essentially of polysilicon.

* * * * *